(12) United States Patent
Rigby

(10) Patent No.: US 6,582,702 B2
(45) Date of Patent: Jun. 24, 2003

(54) HERBAL TONIC COMPOSITION THAT IMPROVES RESPIRATION, AIDS IN THE ELIMINATION OF TOXINS AND IMPROVES OVERALL VITALITY

(76) Inventor: Alvin Foster Rigby, PO Box 285, Providenciales (TC)

( * ) Notice: Subject to any disclaimer, the term of this patent is extended or adjusted under 35 U.S.C. 154(b) by 0 days.

(21) Appl. No.: 09/682,022

(22) Filed: Jul. 10, 2001

(65) Prior Publication Data

US 2003/0012796 A1 Jan. 16, 2003

(51) Int. Cl.$^7$ ............................................. A61K 35/78
(52) U.S. Cl. .................. 424/195.18; 424/725; 424/754; 424/757; 424/744; 424/773; 424/774; 424/775; 424/778; 424/779; 424/750
(58) Field of Search ............................ 424/725, 195.18, 424/754, 757, 744, 773, 774, 775, 778, 779, 750

*Primary Examiner*—Christopher R. Tate
*Assistant Examiner*—Michele C. Flood

(57) ABSTRACT

An herbal composition comprised of extracts from the following herbs: Garlic (*Allium Sativum*), Onion (*Allium Cepa*), Cat Claw (*Macfadyena Unguis-cati*), Rat Root (*Chicocca Alba*), Pear Leaf (*Persea Americana*), Billyweb Bark (*Sweetia Panamensis*), Strongback (*Desmodium Abscendens*), Aloe (*Aloe Barbadensis*), Life Leaf (*Bryophyllum Pinnatum*), Sarsaparilla (*Smilax Officinalis*), Bamboo (*Aralia Mubicaulis*), Geritout (*Pluchea Symphytofolia*), Hibiscus (*Hibiscus Rosa-sinensis*), Balsam (*Myroxylon Balsamum*). The composition acts as a tonic to improve respiration, aid in the elimination of toxins and improves overall vitality.

1 Claim, No Drawings

HERBAL TONIC COMPOSITION THAT IMPROVES RESPIRATION, AIDS IN THE ELIMINATION OF TOXINS AND IMPROVES OVERALL VITALITY

BACKGROUND OF INVENTION

1. Field of the Invention

The present invention relates to ingestible herbal compositions for the improvement of respiration, to aid in the elimination of toxins and improvement of overall vitality.

2. Description of the Related Art

The use of herbs and plants to treat ailments and generally improve overall health has become commonplace. The use of the singular herbs comprising this invention has been documented. A summary of each herb's individual use is described hereafter.

Garlic—(*Allium Sativum*)Commonly used as an antiseptic, anti-cough and promote circulation, as described in many herbal texts. Garlic cloves are obtained at the local supermarket and/or from local gardens. The plant is commonly available throughout North America and the Caribbean.

Onion—(*Allium Cepa*)Commonly used to act as an antibacterial and cough suppressant as described in herbal texts. Onions are obtained at the local market or from the garden. The plant is commonly available throughout North America and the Caribbean.

Cat Claw—(*Macfadyena Unguis-cati*)Commonly used to act as a blood purifier and aid in toxin removal as described in herbal texts. Cat's claw is a vine that grows wild in forests and bush of Barbados and other Caribbean islands.

Rat Root—(*Chicocca Alba*)Commonly used to increase energy and endurance as described in herbal texts. Rat Root grows throughout most of the Caribbean. It is found in abundance on North Caicos and Providenciales of the Turks & Caicos Islands.

Pear Leaf—(*Persea Americana*)Commonly used as an anti-cough ingredient as listed in the herbal texts. It grows wild in many parts of the Caribbean, namely Belize and Barbados.

Billyweb Bark—(*Sweetia Panamensis*)Commonly used as an anti-cough agent and blood purifier as in herbal texts. This bush/tree that grows wild in areas such as Belize and other Caribbean islands.

Strongback—(*Desmodium Abscendens*)Commonly used to relieve muscle and joint pains as in herbal texts. This plant grows wild in the Caribbean, namely Belize, Barbados and Trinidad.

Aloe—(*Aloe Barbadensis*)Commonly used to alleviate ulcers and rheumatism type pains as listed in texts. Aloe grows wild throughout the Caribbean area. The plant can usually be found as a houseplant within North America.

Life leaf—(*Bryophyllum Pinnatum*)Commonly used to aid in expulsion of toxins through the urine and combat shortness of breath as listed in the texts. Life leaf grows wild in scrub area throughout the Caribbean. It is commonly found in the Bahamas, Turks & Caicos and Belize.

Sarsaparilla—(*Smilax Officinalis*)Commonly used to act as a diuretic, tonic and expectorant as described in the texts. Sarsaparilla grows wild throughout the Caribbean. It prefers sandy loam soil. The vine-like growth produces a large root that grows horizontally within the soil.

Bamboo—(*Aralia Mubicaulis*)Commonly used to act as an expectorant and removal of toxins as listed in the texts. Bamboo grows wild in the Caribbean and is sometimes cultivated by homeowners.

Geritout—(*Pluchea Symphytofolia*)Commonly used to act as a decongestant and alleviate "cold type" symptoms as described in texts. Geritout grows wild throughout the Caribbean basin.

Hibiscus—(*Hibiscus Rosa-sinensis*)Commonly used to act in removing toxins and purifying the blood as listed in herbal texts. Hibiscus grows readily in the Caribbean area. Most commonly, it is commonly cultivated by resorts and hotels as a hedge or bush with a red trumpet-shaped flower.

Balsam—(*Myroxylon Balsamum*)Commonly used to promote wound healing as described in texts. The plant grows fairly well throughout the Caribbean, notably in Belize.

All of the invention's herbs have been used by themselves or in various combinations with others. Although these prior art combinations are useful, none has proven to be entirely effective. Furthermore, there is presently no known composition which includes all fourteen herbal extracts of this invention which provides the combination of benefits associated with each individually. Specifically, there is no known ingestible herbal composition which effectively improves respiration, aids in elimination of toxins and improves overall vitality.

Accordingly, there is a need in the art for an ingestible herbal composition which effectively improves respiration, aids in elimination of toxins and improves overall vitality. The present invention is particularly suited to overcome those problems which remain in the art in a manner not previously known. Not only does the composition of the present invention effectively provide the combination of benefits associated with the individual herbal extracts, but the beneficial effects previously associated with each individually have been found to be enhanced. Specifically, it is believed that the composition of the present invention improves respiration, aids in elimination of toxins and improves overall vitality not previously accomplished by the herbs individually.

SUMMARY OF INVENTION

The present invention is directed towards a new and improved ingestible composition for the improvement of respiration, to aid in elimination of toxins and improvement of overall vitality. The composition includes extracts of Garlic (*Allium Sativum*), Onion (*Allium Cepa*), Cat Claw (*Macfadyena Unguis-cati*), Rat Root (*Chicocca Alba*), Pear Leaf (*Persea Americana*), Billyweb Bark (*Sweetia Panamensis*), Strong back (*Desmodium Abscendens*), Aloe (*Aloe Barbadensis*), Life Leaf (*Bryophyllum Pinnatum*), Sarsaparilla (*Smilax Officinalis*), Bamboo (*Aralia Mubicaulis*), Geritout (Pluchea Symphytofolia), Hibiscus (*Hibiscus Rosa-sinensis*), Balsam (*Myroxylon Balsamum*) in combination.

It is an object of the present invention to provide a new and improved ingestible composition for the improvement of respiration.

It is another object of the present invention to provide a new and improved ingestible composition to aid in the elimination of toxins.

It is another object of the present invention to provide a new and improved ingestible composition to improve the person's vitality.

It is yet a further object of the present invention to provide a new and improved ingestible composition which comprises only natural ingredients.

These and other objectives and advantages of the present invention will become readily apparent in the description which follows.

DETAILED DESCRIPTION

The present invention is directed towards a new and improved ingestible composition for the improvement of respiration, to aid in elimination of toxins and improvement of overall vitality. The composition includes extracts of Garlic (*Allium Sativum*), Onion (*Allium Cepa*), Cat Claw (*Macfadyena Unguis-cati*), Rat Root (*Chicocca Alba*), Pear Leaf (*Persea Americana*), Billyweb Bark (*Sweetia Panamensis*), Strongback (*Desmodium Abscendens*), Aloe (*Aloe Barbadensis*), Life Leaf (*Bryophyllum Pinnatum*), Sarsaparilla (*Smilax Officinalis*), Bamboo (*Aralia Mubicaulis*), Geritout (*Pluchea Symphytofolia*), Hibiscus (*Hibiscus Rosa-sinensis*), Balsam (*Myroxylon Balsamum*) in combination.

The preferred method of manufacture of the invention is as follows.

Garlic—(*Allium Sativum*)Purpose in the mix is as an antiseptic, anti-cough and promote circulation, as described in many herbal texts.

Garlic cloves are obtained at the local supermarket and/or from local gardens. The cloves are separated from the bulbs and slightly crushed to break the covering skin. One ounce by weight is placed into 2¼ quarts of water and slowly brought to a boil. The mix is stirred and low boiled for 15 minutes. At the end of this time, it is covered and placed aside to cool to room temperature.

Once being cool enough to handle easily, the liquid is filtered though a screen mesh of 1 mm hole size. A measured 2 quarts of this liquid is set aside to be mixed with the other ingredients later.

Onion—(*Allium Cepa*)Purpose in the mix is to act as an antibacterial and cough suppressant as described in herbal texts.

Onions are obtained at the local market or from the garden. They are peeled of their dry skin and cut into quarters or eights. One ounce of onion by weight is placed in 2¼ quarts of water and slowly brought to a boil. The mix is stirred and low boiled for 15 minutes. At the end of this time, it is covered and placed aside to cool to room temperature.

Once being cool enough to handle easily, the liquid is filtered though a screen mesh of 1 mm hole size. A measured 2 quarts of this liquid is set aside to be mixed with the other ingredients later.

Cat Claw—(*Macfadyena Unguis-cati*)Purpose in the mix is to act as a blood purifier and aid in toxin removal as described in herbal texts.

Cat's claw is a vine that grows wild in forests and bush of Barbados. The whole vine is clipped and cut into ½ inch long sections and allowed to air dry. One ounce by weight is placed into 2¼ quarts of water and slowly brought to a boil. The mix is stirred and low boiled for 15 minutes. At the end of this time, it is covered and placed aside to cool to room temperature.

Once being cool enough to handle easily, the liquid is filtered though a screen mesh of 1 mm hole size. A measured 2 quarts of this liquid is set aside to be mixed with the other ingredients later.

Rat Root—(*Chicocca Alba*)Purpose in the mix is to increase energy and endurance as described in herbal texts.

Rat Root grows throughout most of the Caribbean. It is found in abundance on North Caicos and Providenciales of the Turks & Caicos Islands. The plant root is harvested from the ground and allowed to air dry. It is then cut into ½ inch pieces. Larger sections may be cut again. One ounce by weight is placed into 2¼ quarts of water and slowly brought to a boil. The mix is stirred and low boiled for 15 minutes. At the end of this time, it is covered and placed aside to cool to room temperature.

Once being cool enough to handle easily, the liquid is filtered though a screen mesh of 1 mm hole size. A measured 2 quarts of this liquid is set aside to be mixed with the other ingredients later.

Pear Leaf—(*Persea Americana*)Purpose in the mix is as an anti-cough ingredient as listed in the herbal texts. The leaf of the plant is best used when fresh, although dried may be substituted. It grows wild in many parts of the Caribbean, namely Belize and Barbados. The leaves are cut into smaller portions and one ounce by weight is placed into 2¼ quarts of water and slowly brought to a boil. The mix is stirred and low boiled for 15 minutes. At the end of this time, it is covered and placed aside to cool to room temperature.

Once being cool enough to handle easily, the liquid is filtered though a screen mesh of 1 mm hole size. A measured 2 quarts of this liquid is set aside to be mixed with the other ingredients later.

Billyweb Bark—(*Sweetia Panamensis*)Purpose in the mix is as an anti-cough agent and blood purifier as in herbal texts.

The bark is removed from this bush/tree that grows wild in areas such as Belize, and is allowed to air dry. The bark is then cut up into pieces no larger than 1 inch square. One ounce by weight is placed into 2¼ quarts of water and slowly brought to a boil. The mix is stirred and low boiled for 15 minutes. At the end of this time, it is covered and placed aside to cool to room temperature.

Once being cool enough to handle easily, the liquid is filtered though a screen mesh of 1 mm hole size. A measured 2 quarts of this liquid is set aside to be mixed with the other ingredients later.

Strongback—(*Desmodium Abscendens*)Purpose in mix is to relieve muscle and joint pains as in herbal texts.

The root of this plant that grows wild in the Caribbean, namely Belize, Barbados and Trinidad, is harvested and let air dry. It is then cut up into 2 inch sections and one ounce by weight is placed into 2¼ quarts of water and slowly brought to a boil. The mix is stirred and low boiled for 15 minutes. At the end of this time, it is covered and placed aside to cool to room temperature.

Once being cool enough to handle easily, the liquid is filtered though a screen mesh of 1 mm hole size. A measured 2 quarts of this liquid is set aside to be mixed with the other ingredients later.

Aloe—(*Aloe Barbadensis*)Purpose in mix is to alleviate ulcers and rheumatism type pains as listed in texts.

Aloe grows wild throughout the Caribbean area. The plant leaf/stalks are harvested fresh. Being a succulent, they do not dry well. The leaf/stalks are cut up into 2 to 1 inch sections and one ounce by weight is placed into 2¼ quarts of water and slowly brought to a boil. The mix is stirred and low boiled for 15 minutes. At the end of this time, it is covered and placed aside to cool to room temperature.

Once being cool enough to handle easily, the liquid is filtered though a screen mesh of 1 mm hole size. A measured 2 quarts of this liquid is set aside to be mixed with the other ingredients later.

Life leaf—(*Bryophyllum Pinnatum*)Purpose in mix is to aid in expulsion of toxins through the urine and combat shortness of breath as listed in the texts.

Life leaf grows wild in scrub area throughout the Caribbean. It is commonly found in the Bahamas, Turks & Caicos and Belize. The leaf of the plant is collected and may be used fresh or dried, although fresh is considered more potent. The leaves may be cut up or used whole. One ounce by weight is placed into 2¼ quarts of water and slowly brought to a boil. The mix is stirred and low boiled for 15 minutes. At the end of this time, it is covered and placed aside to cool to room temperature.

Once being cool enough to handle easily, the liquid is filtered though a screen mesh of 1 mm hole size. A measured 2 quarts of this liquid is set aside to be mixed with the other ingredients later.

Sarsaparilla—(*Smilax Officinalis*)Purpose in the mix is to act as a diuretic, tonic and expectorant as described in the texts.

Sarsaparilla grows wild throughout the Caribbean. It prefers sandy loam soil. The vine-like growth produces a large root that grows horizontally in the soil. This root is harvested and let air dry. It then is sectioned into about ½ inch to 1 inch cubes. One ounce by weight is placed into 2¼ quarts of water and slowly brought to a boil. The mix is stirred and low boiled for 15 minutes. At the end of this time, it is covered and placed aside to cool to room temperature.

Once being cool enough to handle easily, the liquid is filtered though a screen mesh of 1 mm hole size. A measured 2 quarts of this liquid is set aside to be mixed with the other ingredients later.

Bamboo—(*Aralia Mubicaulis*)Purpose in the mix is to act as an expectorant and removal of toxins as listed in the texts.

Bamboo grows wild in the Caribbean and is sometimes cultivated by homeowners. Only the tender new shoots with leaves are harvested. These may be air dried or used fresh. As the shoots are tender, no dicing is needed. One ounce by weight is placed into 2¼ quarts of water and slowly brought to a boil. The mix is stirred and low boiled for 15 minutes. At the end of this time, it is covered and placed aside to cool to room temperature.

Once being cool enough to handle easily, the liquid is filtered though a screen mesh of 1 mm hole size. A measured 2 quarts of this liquid is set aside to be mixed with the other ingredients later.

Geritout—(*Pluchea Symphytofolia*)Purpose in mix is to act as a decongestant and alleviate "cold type" symptoms as described in texts. Geritout grows wild throughout the Caribbean basin. The root and leaf of the plant are harvested and let air dry. Both are cut into smaller ½ to 1 inch pieces and equal parts of each amounting to one ounce by weight is placed into 2½ quarts of water and slowly brought to a boil. The mix is stirred and low boiled for 15 minutes. At the end of this time, it is covered and placed aside to cool to room temperature.

Once being cool enough to handle easily, the liquid is filtered though a screen mesh of 1 mm hole size. A measured 2 quarts of this liquid is set aside to be mixed with the other ingredients later.

Hibiscus—(*Hibiscus Rosa-sinensis*)Purpose in mix is to act in removing toxins and purifying the blood as listed in herbal texts.

Hibiscus grows readily in the Caribbean area. Most commonly, it is cultivated by resorts and hotels as a hedge or bush with a red trumpet-shaped flower. The terminal ends of the stem with flowers and leaves are harvested. They may be dried or used fresh. The pieces are cut up into smaller sections about 1 inch long and one ounce by weight is placed into 2¼ quarts of water and slowly brought to a boil. The mix is stirred and low boiled for 15 minutes. At the end of this time, it is covered and placed aside to cool to room temperature.

Once being cool enough to handle easily, the liquid is filtered though a screen mesh of 1 mm hole size. A measured 2 quarts of this liquid is set aside to be mixed with the other ingredients later.

Balsam—(*Myroxylon Balsamum*)Purpose in the mix is to promote wound healing as described in texts.

The plant grows fairly well throughout the Caribbean, notably in Belize. The bark is harvested from the plant and allowed to air dry. It is cut or broken into smaller pieces from ½ to 1 inch long. One ounce by weight is placed into 2¼ quarts of water and slowly brought to a boil. The mix is stirred and low boiled for 15 minutes. At the end of this time, it is covered and placed aside to cool to room temperature.

Once being cool enough to handle easily, the liquid is filtered though a screen mesh of 1 mm hole size. A measured 2 quarts of this liquid is set aside to be mixed with the other ingredients later.

The strained and cooled liquid from the processes outlined above are then placed together into a suitable container (glass or plastic) and vigorously shaken. The mix is then kept refrigerated. It is shaken each time prior to dispensing.

DOSAGE AND USE Instructions for use-Remove the mix from the refrigerator, shake thoroughly. Decant ½ ounce (15 ml) by volume. Take orally. May be mixed or followed with water to improve palatability. Repeat dose up to 3 times a week, depending upon condition. As condition improves, gradually reduce frequency of ½ ounce (15 ml) doses to twice a month. Continue at that dose level indefinitely, or as needed. Children under 12 should receive only ½ dose (7.5 ml) using similar time intervals between doses.

No adverse side effects are reported in the literature at the dosages indicated herein for the listed components.

Various changes may be made within the spirit and scope of the invention as described above.

What is claimed is:

1. An ingestible herbal composition which acts as a tonic to improve respiration, aid in the elimination of toxins and improves overall vitality, comprising equal quantities of extracts from the following herbs:

Garlic (*Allium Sativum*) extract ranging from 2.0 ml to 2.5 ml;

Onion (*Allium Cepa*) extract ranging from 2.0 ml to 2.5 ml;

Cat Claw (*Macfadyena Unguis-cati*) extract ranging from 2.0 ml to 2.5 ml;

Rat Root (*Chicocca Alba*) extract ranging from 2.0 ml to 2.5 ml;

Pear Leaf (*Persea Americana*) extract ranging from 2.0 ml to 2.5 ml;

Billyweb Bark (*Sweetia Panamensis*) extract ranging from 2.0 ml to 2.5 ml;

Strongback (*Desmodium Abscendens*) extract ranging from 2.0 ml to 2.5 ml;

Aloe (*Aloe Barbadensis*) extract ranging from 2.0 ml to 2.5 ml;

Life Leaf (*Bryophyllum Pinnatum*) extract ranging from 2.0 ml to 2.5 ml;

Sarsaparilla (*Smilax Officinalis*) extract ranging from 2.0 ml to 2.5 ml;

Bamboo (*Aralia Mubicaulis*) extract ranging from 2.0 ml to 2.5 ml;

Geritout (*Pluchea Symphytofolia*) extract ranging from 2.0 ml to 2.5 ml;

Hibiscus (Hibiscus *Rosa-sinensis*)extract ranging from 2.0 ml to 2.5 ml; and

Balsam (*Myroxylon Balsamun*) extract ranging from 2.0 ml to 2.5 ml.

\* \* \* \* \*